US00PP31456P2

(12) United States Plant Patent
Korlipara

(10) Patent No.: US PP31,456 P2
(45) Date of Patent: Feb. 18, 2020

(54) ***LEUCANTHEMUM* PLANT NAMED 'SHORTSTOP'**

(50) Latin Name: ***Leucanthemum* x *superbum***
Varietal Denomination: Shortstop

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,963

(22) Filed: Feb. 4, 2019

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
See application file for complete search history.

*Primary Examiner* — Susan McCormick Ewoldt
(74) *Attorney, Agent, or Firm* — Klarquist Sparkman, LLP

(57) ABSTRACT

A new and distinct *Leucanthemum* plant named 'Shortstop' characterized by semi-double daisy type inflorescences, yellow flower buds and young ray florets, fully open inflorescences displaying white ray florets around a large gold disc, excellent bloom number, a medium low, compact habit, and excellent vigor.

1 Drawing Sheet

Botanical denomination: *Leucanthemum* x *superbum*.
Variety designation: 'Shortstop'.

BACKGROUND

The present invention relates to a new and distinct cultivar of *Leucanthemum* x *superbum* given the cultivar name 'Shortstop'. *Leucanthemum* is in the family Asteraceae. *Leucanthemum* 'Shortstop' originated from a controlled cross between unnamed, proprietary *Leucanthemum* x *superbum* seedlings. The seed of many crosses was massed so the exact parents are unknown.

Compared to *Leucanthemum* 'Whoops-a-Daisy', U.S. Plant Pat. No. 27,259, the new plant has semi-double inflorescences rather than single.

Compared to *Leucanthemum* 'Snowcap', an unpatented plant, the new plant has yellow colored flower buds rather than white and is semi-double rather than single.

Compared to *Leucanthemum* 'Snowbound', U.S. Plant Pat. No. 25,929, the new plant is shorter and is semi-double rather than single.

SUMMARY

This new *Leucanthemum* cultivar is distinguished as unique with its:

1. semi-double daisy type inflorescences,
2. yellow flower buds and young ray florets,
3. fully open inflorescences that display white ray florets around a large gold disc,
4. excellent bloom number,
5. medium low, compact habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

The foregoing and other objects, features, and advantages of the invention will become more apparent from the following detailed description, which proceeds with reference to the accompanying figures.

BRIEF DESCRIPTION OF THE DRAWINGS

FIG. 1 shows a one-year-old plant growing in the ground in full sun in the trial field in mid-July in Canby, Oreg.

FIG. 2 shows a one-year-old plant growing in the ground in full sun in the trial field in mid-July in Canby, Oreg.

DETAILED DESCRIPTION

The following is a detailed description of the new *Leucanthemum* cultivar based on observations of a 3-year-old specimen growing in the field in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart*, $5^{th}$ edition, 2007.

Plant:

*Type*.—Herbaceous perennial.
*Hardiness*.—USDA Zones 5 to 9.
*Size*.—Grows up to 72 cm wide and 30 cm tall to top of inflorescences.
*Form*.—Basal clump.

*Number of crowns.*—90.
*Vigor.*—Excellent.

Stem (flowering):
*Type.*—Ascending with thick stems.
*Number of stems.*—About 180 stems from the crown, each flowering with 1 to 4 flowers per stem.
*Stem strength.*—Strong.
*Size.*—Grows to about 26 cm to a terminal inflorescence and 6 mm wide at base.
*Internode length.*—1 to 2 cm.
*Surface texture.*—Pubescent.
*Color.*—Green 137A.

Leaves:
*Type.*—Simple.
*Shape.*—Lanceolate.
*Arrangement.*—Alternate.
*Blade size.*—Grows to 6.6 cm long and 16 mm wide.
*Margins.*—Coarsely serrate.
*Apex.*—Acute.
*Base.*—Clasping.
*Surface texture.*—Pubescent on both sides.
*Venation.*—Pinnate.
*Petiole.*—Sessile.
*Color.*—Topside and veins between Green N137A and Green 137A, bottom side Yellow Green147B with main vein Yellow Green 147C.

Inflorescence:
*Type.*—Composite on terminal stalked heads.
*Number of inflorescences per plant.*—About 180.
*Size.*—Grows to 7.5 cm wide and 4 cm deep.
*Form.*—Ray florets held upright when young, lower ray florets reflex down with maturity, mature disc is mostly flat.
*Bud* (*immature inflorescence*).—2.5 cm wide and 2 cm deep, ray florets held vertically and cupped inwards, Yellow Orange 15A.
*Ray florets.*—With 1 pistil and no stamen, about 180 in number, oblong, tip 3 to 5 lobed (lobes 1 mm to 2.5 mm long), margins entire, base attenuate, average size 2.5 cm long and 6 mm wide, glabrous on both sides; limb 1 to 4 cm long, top and bottom side Yellow 5D with tips 4A when young changing to White NN155B; claw 3 mm long and 1.5 mm wide, Yellow Green 144B; pistil 6 mm long, ovary 1.5 mm long, Yellow Green 145D, style 3.5 mm long, Yellow Green 145D, 2 branched stigma 0.5 mm long, Yellow 7A.
*Disc.*—Slightly concave becoming flat, becoming 8 mm deep and 2.3 cm wide with maturity, Yellow Orange 16A.
*Disc florets.*—About 80 in number, each 7 mm long and 1.2 mm wide; corolla tubular campanulate, 6 mm long and 1 mm wide, 5 lobed, glabrous, Yellow 13A on top half and Yellow Green 145A on the bottom half; pistil 1, 5 mm long, ovary 1 mm long and Yellow Green 145D, style 3 mm long, Greyed Yellow 160B, 2 branched stigma 0.5 mm long, Greyed Yellow 160B; stamen 5 in number, 5 mm long, filaments 2 mm long, Yellow Green 150D, anthers 2.5 mm, Yellow Orange 17A, pollen Yellow Orange 21A.
*Involucral bracts.*—About 45 in number, in 3 imbricate whorls, area 3.1 cm wide and 8 mm deep, lobes lanceolate, grow to 11 mm long and 4 mm wide, Green 137A, margin thin and somewhat transparent, Greyed Purple 187A, tip acute, glabrous.
*Receptacle.*—Grows to 18 mm wide and 5 mm deep, Yellow Green 145C.
*Bloom period.*—June through July in Canby, Oreg.
*Fragrance.*—None.
*Lastingness.*—Each inflorescence lasts about three weeks in Canby, Oreg.

Seeds: None seen.
*Fertility.*—Low.

Disease and pests: The new cultivar is typical to the genus. No known resistances to pests or diseases. No problems have been found in Canby, Oreg.

I claim:

1. A new and distinct *Leucanthemum* plant as herein illustrated and described.

* * * * *

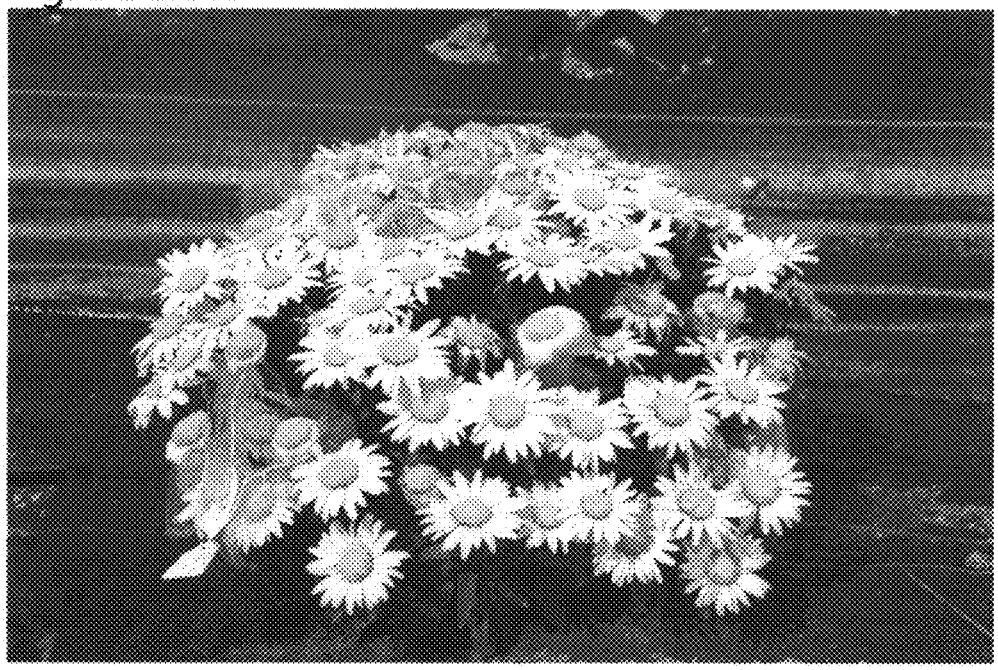

Fig.1 Below
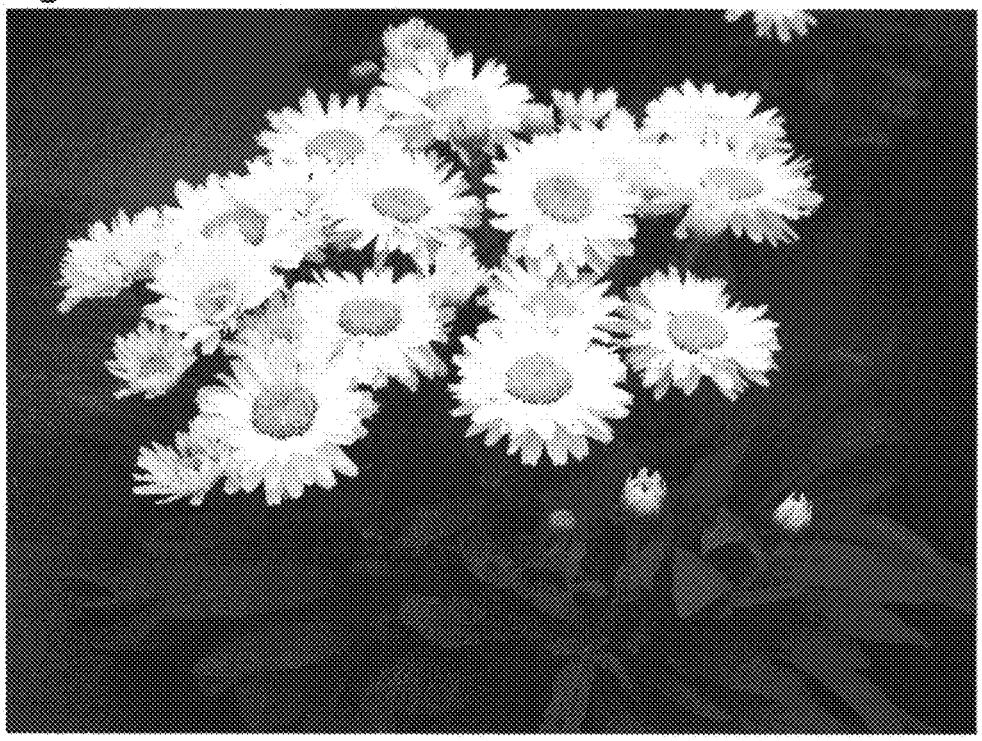
Fig. 2 Below